(12) United States Patent
Montgomery

(10) Patent No.: US 8,986,005 B2
(45) Date of Patent: Mar. 24, 2015

(54) STRIP FOR TRANSFERRING A THERAPEUTIC COMPOSITION TO A TOOTH

(75) Inventor: R. Eric Montgomery, Eindhoven (NL)

(73) Assignee: Discus Dental, LLC, Culver City, CA (US)

( * ) Notice: Subject to any disclaimer, the term of this patent is extended or adjusted under 35 U.S.C. 154(b) by 0 days.

(21) Appl. No.: 13/821,401

(22) PCT Filed: Sep. 12, 2011

(86) PCT No.: PCT/US2011/051240
§ 371 (c)(1),
(2), (4) Date: Jun. 4, 2013

(87) PCT Pub. No.: WO2012/034127
PCT Pub. Date: Mar. 15, 2012

(65) Prior Publication Data
US 2013/0266914 A1    Oct. 10, 2013

Related U.S. Application Data

(60) Provisional application No. 61/382,000, filed on Sep. 12, 2010.

(51) Int. Cl.
*A61C 19/00* (2006.01)
*A61C 19/06* (2006.01)
*A61K 9/00* (2006.01)

(52) U.S. Cl.
CPC .............. *A61C 19/066* (2013.01); *A61C 19/063* (2013.01); *A61K 9/0053* (2013.01)
USPC ............................................ 433/80; 424/435

(58) Field of Classification Search
USPC ............ 433/80; 132/321, 323; 424/435, 443, 424/447
See application file for complete search history.

(56) References Cited

U.S. PATENT DOCUMENTS

| 2,673,364 | A | * | 3/1954 | Diveley ........................... 132/286 |
| 4,941,487 | A | * | 7/1990 | VanBeneden .................. 132/323 |
| 5,538,732 | A | * | 7/1996 | Smith et al. .................... 424/402 |
| 6,001,380 | A | * | 12/1999 | Smith et al. .................... 424/402 |
| 6,145,516 | A | * | 11/2000 | Guay et al. ..................... 132/321 |
| 6,649,147 | B1 | * | 11/2003 | Ye et al. ............................ 424/49 |
| 7,192,280 | B2 | * | 3/2007 | Allred et al. .................... 433/215 |
| 7,645,137 | B2 | * | 1/2010 | Wasyluch ......................... 433/29 |
| 2005/0260544 | A1 | * | 11/2005 | Jones et al. ................. 433/217.1 |

* cited by examiner

*Primary Examiner* — Ralph Lewis

(57) ABSTRACT

An oral care device is described for contacting or transferring a dental composition to the hard or soft surfaces of the teeth comprising a backing layer and a discontinuous pattern of a dentally therapeutic composition. A method of using said oral care device to effectuate an aesthetic or therapeutic treatment is also described, whereby the oral care device is placed against the surface of at least one oral cavity structure, the discontinuous pattern of dentally therapeutic composition is contacted with or transferred to said structure. The backing layer may be left in place during the treatment period, or optionally removed from the oral cavity while leaving the therapeutic composition in contact with the target structure.

21 Claims, 3 Drawing Sheets

US 8,986,005 B2

STRIP FOR TRANSFERRING A THERAPEUTIC COMPOSITION TO A TOOTH

BACKGROUND OF THE INVENTION

For years, dental compositions such as tooth whiteners and fluoride gels have been applied to the teeth of patients in need of a cosmetic or therapeutic dental treatment. These compositions, usually in the form of a gel, paste or foam, have traditionally been comprised of one or more active therapeutic agents dissolved in an aqueous or water-soluble carrier. An aqueous or water-soluble carrier was used because the majority of dental therapeutic agents, such as inorganic fluorides (anticaries agents), peroxides (tooth whitening agents), chlorhexidine (an antibacterial agent), potassium nitrate (a tooth desensitizing agent) and polyphosphates (tartar control agents) are water-soluble compounds. Most of these compositions are intended to be brushed, rinsed or sprayed onto the teeth for a short period of time, for instance the few minutes during which the average individual will brush his or her teeth.

A number of dental treatments, though, require that a therapeutic agent be in contact for a much longer period of time than is practical by the above methods. Arch-shaped dental trays have been developed that are either customized by methods known in the art, or are in the one-size-fits-all category. Such trays are typically loaded with a small amount of a dental composition, and then placed over the teeth of the upper arch, the lower arch, or both arches simultaneously (using two dental trays at the same time). While such devices and methods tend to greatly increase the length of time a dental composition remains in contact with the tooth surfaces, said compositions still remain highly soluble in water. Being soluble in water, these compositions rapidly dissolve and leach out of the dental tray once placed in the mouth in contact with saliva. Upon dilution, these compositions are seen to quickly migrate out of the dental tray and thus become free to contact areas of the oral cavity not intended for treatment. The diluted compositions may also be swallowed by the patient, for instance when a tooth whitening composition is loaded into a dental tray and placed in the oral cavity against the teeth for an extended period of time, such as overnight while the patient is asleep. The whitening composition within the tray gradually becomes lower in viscosity due to dilution with saliva, migrates out of the dental tray, and is unintentionally swallowed by the patient. Repeated ingestion of the oxidizing ingredients of such compositions may be detrimental to the tissue surfaces of the digestive tract.

Other delivery modes for applying tooth whitening compositions to the surfaces of the teeth are available, each with different degrees of acceptance by the consumer and effectiveness. There exists thin plastic strips that are coated on one side with a layer of tooth whitening gel and stored until use against a release backing (similar to that used for a pressure sensitive label), in a unit dose laminated pouch. When a consumer or patient desires tooth whitening, the pouch is opened, the strip/gel device combination is removed from the release backing, and the user carefully places the strip on the teeth to be whitened (gel side against the teeth). While this approach has been shown to be safe and effective, the strips are somewhat cumbersome to handle and position, and there are instances where the entire plastic strip and associated gel have been swallowed by the consumer. Furthermore, the strip of plastic must be removed at some point in time, typically 20-45 minutes following initial placement against the teeth, and following removal of the strip the patient will have to dispose of the strip and often rinse their mouth to remove excess whitening gel. This can be inconvenient if done anywhere other than in the privacy of one's home or office. If the tooth whitening gel is also completely water soluble, salivary intrusion and gel dissolution can occurs in a similar fashion to that observed with dental whitening trays. An additional drawback of these strips is that the hydrogen peroxide active ingredient in the gel tends to degrade faster over time as a thin layer, due to the relationship of hydrogen peroxide stability to surface area/volume ratios. In general, a high surface area to volume ratio leads to more rapid degradation of hydrogen peroxide, said high ratio being inherent in the thin layer of tooth bleaching gel deposited on the backing material of these strips.

Efforts have been made to reduce the perceptibility of dental devices placed in the oral cavity to deliver therapeutic compositions to the tooth and gum surfaces, however to date the trade-offs made in order to improve patient compliance and comfort have resulted in products that do not perform as well as the traditional and more cumbersome methods, such as custom tray-administered tooth whitening. Brush-on products, while being simple to use and easy to apply, may dissolve or erode quickly after being deposited on the tooth surfaces and therefore are not as effective as products that remain in contact with the tooth surfaces for extended periods of time.

SUMMARY OF INVENTION

The present invention relates to devices for applying a therapeutic dental composition in a physical form that may be directly applied to an oral cavity surface, such as a dental wipe or transfer strip, thus obviating the need for a dental tray or other such delivery device.

The present invention still further relates to methods of applying a therapeutic dental composition in packages that facilitate easy dispensing and application of said compositions into the oral cavity by a patient, dental practitioner, or consumer.

In another aspect of the present invention, a delivery device, such as a wipe or transfer strip, is used to apply dental therapeutic compositions, such as tooth whiteners, directly onto the tooth and/or gum surfaces by a consumer, patient, dentist, or dental practitioner.

In another aspect of the present invention, a delivery device is coated on one side with a discontinuous pattern of a dental therapeutic composition, such as a tooth whitener or a tooth enamel remineralizing agent.

In another aspect of the present invention, a delivery device is coated on one side with a discontinuous layer of a dentally therapeutic composition, such as a tooth whitener or a tooth remineralizing agent, such that the discontinuous layer comprises discrete and unconnected areas of the composition surrounded by connected areas either without the composition or with a different composition.

In yet another aspect of the present invention, a delivery device is coated on one side with a discontinuous layer of a dentally therapeutic composition, such that the discontinuous layer is in the form of a micro-pattern comprising dots or islands of dentally therapeutic composition.

In yet another aspect of the present invention, a delivery device is coated on one side with a discontinuous layer of dentally therapeutic composition in the form of a micro-pattern, such that the micro-pattern comprises discrete dots or islands of the composition that are from about 10 microns to about 2 millimeters in diameter.

In yet another aspect of the present invention, a method of applying a dental therapeutic composition to an oral cavity surface comprises either wiping or pressing a device comprising a backing layer and a patterned therapeutic composition against the oral cavity surface to effectuate transfer of the composition to the oral cavity surface.

In yet another aspect of the present invention, a method of applying a dental therapeutic composition to an oral cavity surface comprises wiping or pressing a device comprising a backing layer and a patterned therapeutic composition against the tooth and gums of a subject, whereby the pressure exerted to transfer said composition is sufficient to transfer the composition to the tooth surface, but insufficient to transfer the composition to the gingival or gum tissues.

In yet another aspect of the present invention, a kit comprises at least one device comprising a backing layer and a patterned therapeutic composition disposed on said backing layer in a discontinuous pattern, and at least one set of instructions.

In yet another aspect of the present invention, the delivery device is coated with a dental therapeutic composition arranged as a discontinuous pattern and dispensed from a dispensing device. The use of a dispensing device allows the user to transfer said composition to the tooth and gums without need to directly manipulate the delivery device with their hands.

DETAILED DESCRIPTION OF THE INVENTION

Figure 1A:
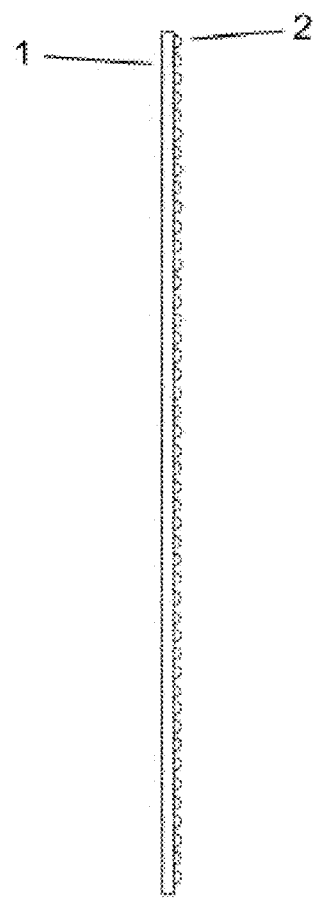
FIG. 1a is a longitudinal cross section of a delivery device of the present invention.
Figure 1B:
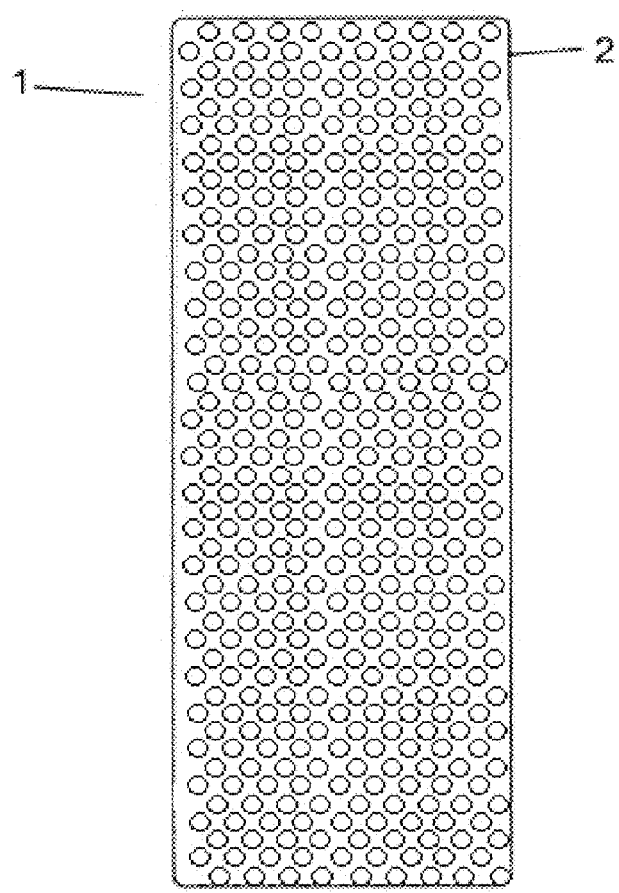
FIG. 1b is a top view of a delivery device of the present invention.

A novel oral care device is described herein that is used to deposit a dentally therapeutic composition onto hard or soft structures in the oral cavity. The fundamental elements of the inventive device are (1) a deformable backing or carrier layer, film, sheet or similar construction that can conform to the shape of at least one tooth surface of a subject and (2) a dentally therapeutic composition deposited on one side of said backing or carrier layer in a discontinuous pattern such that there are discrete areas of said composition that are surrounded by areas that are devoid of said composition. FIG. 1 is an example of such a device. FIG. 1 depicts a thin plastic film that is coated on one side with a discontinuous pattern of a therapeutic composition with adhesive properties that is capable of adhering to the hard surfaces of the teeth. While in some applications it may be desirable for the dentally therapeutic composition to adhere to both the hard surfaces of the teeth and the soft tissue surfaces of the gingival and gums, certain applications, such as tooth whitening, require that the tooth whitening composition adhere only or preferentially to the tooth surfaces to be whitened. Tooth whitening compositions typically comprise one or more oxidizing agents which while effective at oxidizing the staining compounds at or near the tooth surface, are also capable of causing soft tissue irritation when in contact with the gingival or gum tissue. This typically limits the concentration of oxidizing agents in tooth whitening compositions to that which will not cause an undue amount of soft tissue irritation due to incidental contact with the gingival or gums. Such limitation on oxidizer concentration also limits the effectiveness of tooth whitening compositions and extends the period of time required for said compositions to effect a visible improvement in tooth color.

The novel oral care device described herein also provides a means of applying a dentally therapeutic composition preferentially onto hard tooth surfaces while minimizing deposition of the composition onto soft tissue surfaces. It has been discovered that by providing backing or carrier layer coated on one side with a discontinuous layer of a composition capable of adhering to the hard surface of a tooth, upon applying pressure to the side of the backing or carrier layer opposite to the composition, the composition may be transferred preferentially to the hard tooth surface. Such differentiated deposition of a therapeutic composition is not possible with continuous layers of material.

The inventive device described above comprises a backing layer and a micro-patterned composition deposited on one surface of said backing layer.

Dental Device

FIGS. 1a, 1b, 3 and 4 depict an exemplary embodiment of the device. The backing layer 1 is comprised of one or more flexible films that can be easily handled in both continuous manufacturing processes and by the end user. The backing layer film 1 may comprise polymers, elastomers, waxes, natural and synthetic woven materials, non-woven material, and combinations thereof. The backing layer 1 may be a single layer of material or a laminate of more than one layer. Regardless of the number of layers, the backing layer 1 is substantially water insoluble. Preferably, the material is any type of polymer or combination of polymers that meet the required flexural rigidity and are compatible with oral care substances. Suitable polymers include, but are not limited to, poly (ethylene), poly (propylene), poly (ethylene-co-vinyl acetate), polyesters (such as Mylar®), poly (vinyl alcohol) and combinations thereof. Fluoropolymers such as Teflon® are also suitable. The preferable materials are low density poly (ethylene) and film-forming waxes. The backing layer 1 is generally less than about 1 mm thick, preferably less than about 100 microns thick, and more preferably from about 10 microns to about 50 microns thick.

Backing layer 1 constructions that are intended to be used to transfer the micro-patterned therapeutic composition 2 to an oral cavity surface and removed shortly thereafter may also comprise a release layer or coating designed to allow for the efficient transfer of the micro-patterned composition 2 from the backing layer 1 to the tooth surface. The release agent or coating should preferentially provide the side of the backing layer coated with the micro-patterned composition with an adhesive strength to the micro-patterned composition that is less than that of the adhesive strength of the micro-patterned composition 2 to the intended oral cavity substrate target. Typical release agents or coatings are comprised of low-surface tension materials such as waxes, fatty acid metal soaps, long chain alkyl hydrocarbon derivatives, silicone polymers and fluorinated compounds that, when coated onto the backing layer lower the surface energy of the backing layer in contact with the micro-patterned composition. The release agent or coating may also be advantageously selected to adhere to the micro-patterned composition 2 such that it is transferred to the oral cavity on the outer (away from the teeth) surface of the composition, thereby protecting said composition from contact with saliva and extending the residence time on the oral cavity surface.

There are a number of variables which determines the adhesive strength between the micro-patterned composition and the backing layer, as well as the adhesive strength between the micro-patterned composition and the tooth. The selected backing layer 1 may have a lower surface energy than the surface energy of the teeth so that the composition will preferentially bind to the teeth, although other factors such as composition viscosity and specific composition-tooth surface interactions other than surface tension differences can play a role in determining whether the composition will release from the backing. The surface energy of the backing layer can be controlled by choosing a backing layer material with an inherent surface energy that is low enough to release the composition when in contact with a tooth. Alternatively, a backing layer may be coated with a release agent or coating in order to lower the surface energy of the backing layer. Also, certain additives, such as adhesion promoters (see below) can be added to the micro-patterned composition 2 so that the composition adheres more strongly to the teeth than the backing layer 1. Another factor is the pattern of the micro-patterned composition 2. The more surface area occupied by the micro-patterned composition 2 occupies on the backing layer 1 increases the adherence between micro-patterned composition 2 and the backing layer 1. Thus, a strip where the micro-patterned composition 2 is a continuous layer occupying the entire backing layer will adhere more strongly of the backing layer 1 than if the micro-patterned composition 1 is arranged in a discontinuous pattern on the backing layer 1.

Due to the great number of variables involved with the release strength and the adhesive strength, a wide range of compositions and materials can be selected for use. However, the adhesive strength of the composition to the teeth should always be greater than the release strength of the composition to the backing, such that the composition is always transferred from the backing layer to the teeth during use and the backing layer can be easily separated from the composition, leaving the composition on the teeth.

Micro-patterned composition 2 is arranged as a discontinuous layer on backing layer 1. A discontinuous layer of composition means that there are discrete and unconnected areas of composition on the backing layer that is surrounded by areas without composition. Micro-patterned composition 2 can be formed in any number of patterns, as long as the pattern is discontinuous. For example, one embodiment of the micro-patterned composition 2 can be a series of dots or islands of composition. Other possible embodiments of micro-patterned composition 2 include a discontinuous series of squares, stripes or waves.

Figure 2A:
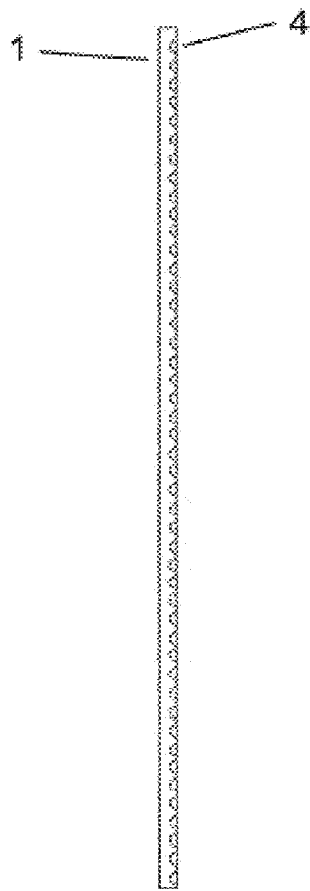
FIG. 2a is a longitudinal cross section of a delivery device of the present invention.
Figure 2B:
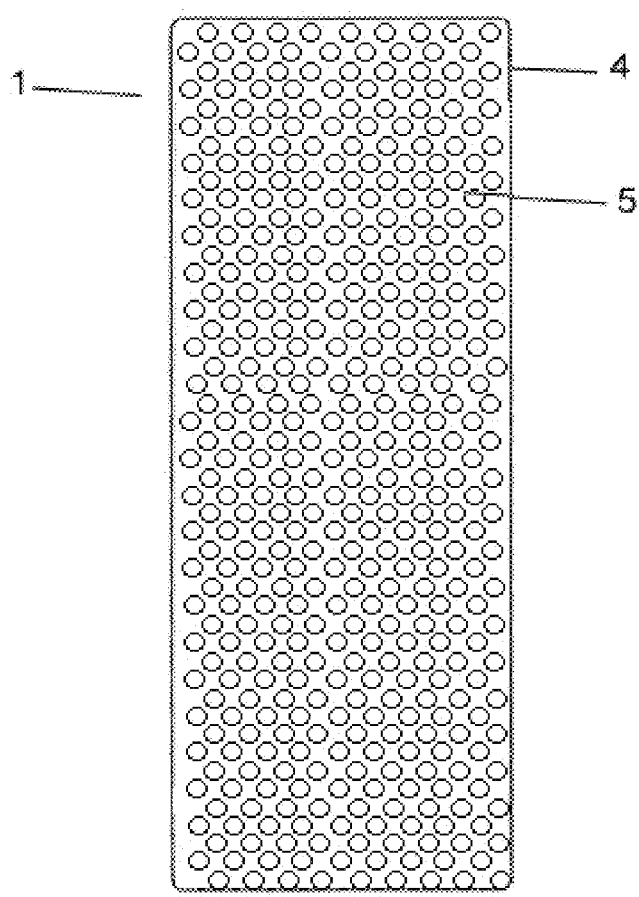
FIG. 2b is a top view of a delivery device of the present invention.

FIGS. 2a-2b depicts an alternate embodiment of the dental device. FIG. 2a is a longitudinal cross section view showing backing layer 1 with a series of wells or pits 4. The wells or pits 4 are filled with composition 5. FIG. 2b shows backing layer 1 with the wells or pits 4 filled with composition 5, which creates a discontinuous micro-pattern of composition.

Figure 1C:
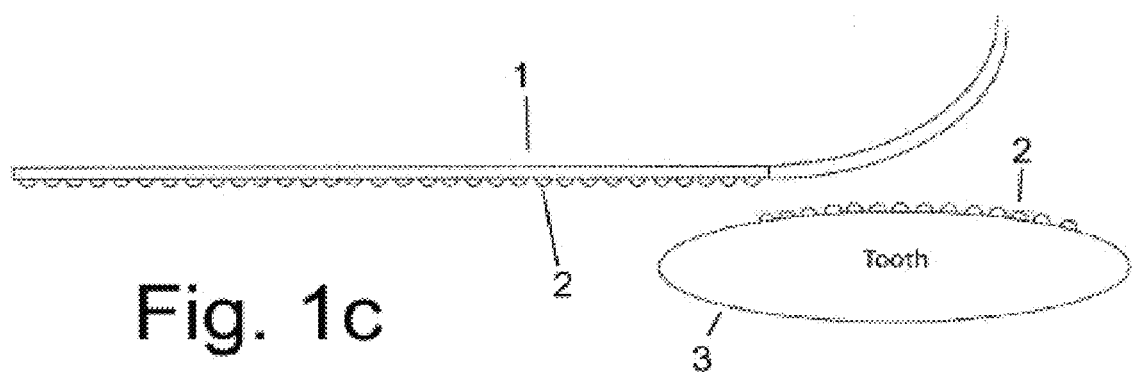
FIG. 1c is a top view of a delivery device depositing composition onto a tooth.
Figure 2C:
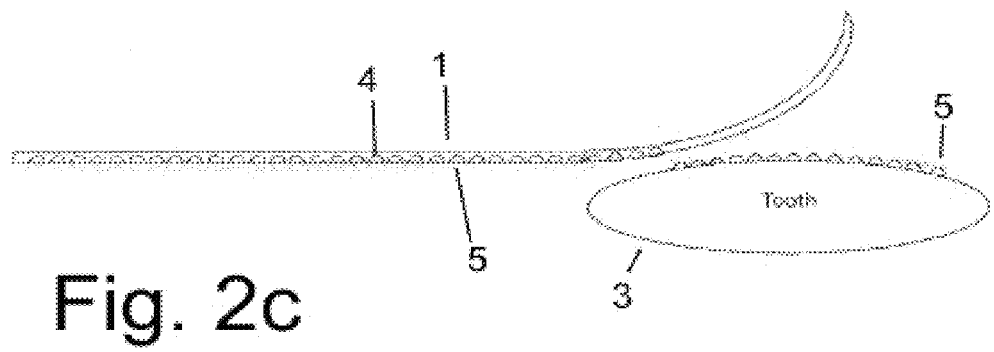
FIG. 2c is a top view of a delivery device depositing composition onto a tooth.

FIGS. 1c and 2c are a depiction of the use of the dental device. In FIG. 1c, the dental device is used by pressing backing layer 1, with micro-patterned composition 2 against teeth 3, onto teeth 3. The pressure from pressing backing layer 1 against the teeth is sufficient pressure to completely transfer the micro-patterned composition 2 that is in contact with the teeth from the backing layer 1 to the teeth 3. With the micro-patterned composition 2 completely transferred to the teeth 3, backing layer 1 can either remain on the teeth 3 or removed. If backing layer 1 is removed from teeth 3, any micro-patterned composition 2 that has been in contact with teeth 3 remains on teeth 3 despite the removal of backing layer 1.

Similarly, in FIG. 2c, the dental device is used by pressing backing layer 1, with micro-patterned composition 2 against teeth 3, onto teeth 3. The pressure from pressing backing layer 1 against the teeth is sufficient pressure to completely transfer the composition 5 that is in contact with the teeth from the backing layer 1 to the teeth 3. With composition 5 completely transferred to the teeth 3, backing layer 1 can either remain on the teeth 3 or removed. If backing layer 1 is removed from teeth 3, any composition 5 that has been in contact with teeth 3 remains on teeth 3 and does not remain in the wells and pits 4 despite the removal of backing layer 1.

In an alternative embodiment, the backing layer could be a part of a dispensing device (not illustrated). In this embodiment, the micro-patterned composition is arranged as a discontinuous layer on a continuous backing layer. The continuous backing layer is then wound around a spool on each end. As the user applies the composition by moving the dispensing device across their teeth, the empty backing layer winds around one spool, while the other spool continues to unwind backing layer with composition.

Therapeutic Compositions

The therapeutic micro-patterned dental composition 2 herein described may be disposed on the surface of the backing layer 1, which is used to apply one or more therapeutic agents to the oral cavity. The dental composition will contain one or more therapeutic agents dispersed in a water-insoluble, water-resistant, or water-soluble carrier, and the therapeutic agents will be released from the carrier over a period of time. The direction of agent release may be towards the oral cavity surface on which it is situated, towards the lumen of the oral cavity, away from the oral cavity surface on which it is situated, or both.

The dental composition of the invention is comprised of a composition that is capable of being dried or otherwise thickened into a solid or semi-solid carrier and at least one therapeutic agent dispersed throughout the carrier. Solid is being defined as not capable of being deformed as a result of the pressure applied to transfer the composition from the backing layer to the tooth. Semi solid is being defined as capable of being permanently deformed as a result of the pressure applied to transfer the composition from the backing layer to the tooth. The therapeutic agent may be dissolved in the carrier or simply dispersed homogeneously in the carrier as an insoluble suspended solid particulate. The therapeutic agent may also be emulsified with the carrier, creating separate and discrete solid carrier and therapeutic agent phases within the composition. The emulsion may be either an agent-in-carrier emulsion or a carrier-in-agent emulsion, analogous to water-in-oil or oil-in water emulsions. The dental composition may also be a solid or semi-solid emulsion with additional phases to those described above.

The therapeutic agent is placed in close proximity to the tissue surface, that is, dispersed or dissolved in a film of the carrier deposited by contacting the inventive dental composition with said tissue surface. The composition of the carrier can be varied so as to provide the dental composition with a short, medium, or long residence time on the oral tissue surface. Solubility of the carrier composition in water (or in saliva) is a major predictor of the residence time for the resultant film deposited on an oral cavity surface. Rapidly dissolving films will release therapeutic agents faster than slowly dissolving or water-insoluble films. It may be desirable, in some cases, to prolong release of the therapeutic agent from the film by using a less water-soluble carrier composition; in other cases, quick release of therapeutic agent may be preferred, and a highly water-soluble carrier composition is used. One preferred embodiment is a carrier composition with limited water solubility that will produce deposited micro-patterns on the tooth surface that preferentially release the therapeutic agent towards the tooth onto which the micro-patterned composition is applied.

The micro-patterned composition is in a solid or semi-solid form at room temperature, defined herein as between about 20 and 30 degrees Celsius (C.). Immediately upon or shortly after contact with the oral cavity tissue surface to be treated, the dental composition adheres as a pattern or film, which is also in a solid or semi-solid form. Moisture in the oral cavity may dissolve the film in a short or long time frame, thereby changing the film from a solid or semi-solid to a liquid (i.e. a dissolved or dispersed solid). In any event, the temperature of the oral cavity and its tissue surfaces (between about 30 and 39 degrees C.) should not be sufficient to immediately melt the composition when deposited on the target surface. Therefore, the therapeutic compositions of this invention are preferably solid or semi-solid at temperatures between 20 and 40 degrees C. In some cases, it may be desirable for the composition to be a solid or semi-solid at any temperature up to about 85 degrees C., which is nearing the maximum tolerable temperature for humans drinking hot potable liquids. Compositions with high melting temperatures will be more resistant to liquefaction if subjected to hot potable liquids while the film is in place in the oral cavity.

The present invention describes devices and methods for applying a solid or semi-solid oral therapeutic dental composition comprising: (1) a toxicologically acceptable water-insoluble, water-resistant or water-soluble solid or semi-solid carrier, (2) an orally or dentally therapeutic agent that is dissolved, dispersed, or otherwise homogeneously or heterogeneously distributed throughout said carrier for the purpose of treating a disease, symptom or condition when applied to at least one surface of the oral cavity; and (3) optionally, auxiliary ingredients. Two or more orally or dentally therapeutic agents may be employed within the same composition in order to treat multiple diseases, symptoms or conditions.

The above composition may be applied to one or more surfaces in the oral cavity, such as the teeth, gums or tongue, to affect a therapeutic, curative or cosmetic effect on or around the surface contacted. Once in contact with the surface (tooth, gingival tissue, etc.), the inventive composition may optionally be activated by the moisture in saliva by solubilizing, mobilizing, releasing or otherwise activating the oral care therapeutic agent dispersed in the carrier. The activated therapeutic agent thus slowly migrates out of the film or micro-patterned array, preferably in the direction of the oral cavity surface, and therefore exerts the aforementioned therapeutic or cosmetic effect.

The solid or semi-solid carrier may contain any number of water-insoluble, water-resistant or water-soluble ingredients, including one or more of the following, either alone or in combination: water, glycerin, polyethylene glycol, propylene glycol, diglycerol, hydrogenated vegetable oils, waxes, fatty acid esters of glycerol, fatty acid esters of polyglycerol (including diglycerol esters and polyglycerol-3 esters), fatty acid esters of sugar alcohols (including sorbitan monostearate), fatty acid esters of polyethylene glycol, petrolatum, and other orally acceptable, water-insoluble or water-resistant, solid or semi-solid substances. A water-insoluble carrier will not dissolve in saliva but will eventually be removed from the teeth by mechanical erosion. A water-resistant carrier is resistant to removal by contact with an aqueous solution. A water-insoluble or water-resistant carrier releases all or a substantial portion of the therapeutic agent before being eroded. The therapeutic agent is typically water soluble and is released from the carrier when water permeates into the film. Ingredients, poly (vinyl pyrrolidone) (PVP), for example, may be added to make the carrier more readily absorb water.

Another type of solid or semi-solid water-resistant carrier may be provided which contains a water-soluble fluid, solid or semi-solid, combined with a water-insoluble additive. One such composition comprises a water-soluble or partially water-soluble polyethylene glycol (PEG) fluid, paste or solid matrix that includes one or more additives for rendering it water-resistant. Such additives may include oils, waxes and polymers that possess limited water solubility, but are compatible, soluble, or otherwise dispersible in the PEG fluid, paste or solid. Thus, the combined carrier composition described possesses limited solubility, and has utility in the practice of the overall invention.

Certain carrier embodiments may contain a water-resistant additive comprising a mixture of a high molecular weight water-soluble anionic polymer, such as carboxypolymethylene (Carbopol®, Lubrizol Corporation, Cleveland, Ohio)) or hydrolyzed or unhydrolyzed methyl vinyl ether/maleic anhydride copolymer (Gantrez®, ISP, Wayne, N.J.), either alone or together with a di- or trivalent ion such as calcium, zinc, or aluminum. Such ions may be present in the formulation as inorganic salts (such as calcium phosphate or zinc oxide) or organic salts (such as aluminum oxalate, calcium lactacte or zinc lactate). Upon contact with moisture, the anionic polymer and the di- or trivalent ion become partially or completely solubilized, thereupon forming a water-resistant, crosslinked polymer structure. The resulting water-resistant structure further reduces the solubility of a solid or semi-solid carrier as described above, the result being increased resistance to erosion of the film when attached to an oral cavity surface, such as the teeth or gums. Alternatively, a composition comprising the high molecular weight water-soluble anionic polymer can be applied to the tooth or gum surfaces, and subsequently and sequentially contacted with a second composition comprising a di- or tri-valent ion as described above in order to achieve the same degree of insolubilization of the anionic polymer on the tooth or gum surface.

The use of a water-insoluble or water-resistant carrier further supports stability of the dental composition and therefore lends to a longer shelf-life than compositions not including these carriers. A preferred shelf life ranges from six months to five years.

The concentration of carrier in the composition may be about 10%, 15%, 20%, 25%, 30%, 35%, 40%, 45%, 50%, 55%, 60%, 65%, 70%, 75%, 80%, 85%, 90%, 95%, 96%, 97%, 98%, 99% weight to weight of the composition.

Therapeutic agents useful when applied to the oral cavity include those known to be effective against tooth decay or caries, tartar or calculus, dental plaque, halitosis, tooth stains, gingivitis, periodontal disease, oral ulcers, and other diseases, afflictions or symptoms of the oral cavity. Therapeutic agents may include antimicrobial agents, tooth whiteners, anti-inflammatory agents, tooth desensitizers, anticaries agents, tartar control agents, tooth and gum surface protectants, and tooth stain prevention agents, for example.

Suitable antimicrobial agents known or anticipated to have utility in the inventive compositions include compounds with inhibitory activity against microorganisms found in the oral cavity. Compounds such as triclosan, chlorhexidine salts (such as chlorhexidine digluconate), cetylpyridinium chloride and domiphen bromide are suitable antimicrobial agents useful in the present inventive compositions.

Suitable tooth whitening agents include one or more peroxide-containing compounds, or more broadly, oxidizing compounds. Such oxidizing compounds include alkali metal percarbonates (such as sodium percarbonate), carbamide peroxide, sodium perborate, potassium persulfate, calcium peroxide, zinc peroxide, chlorine dioxide, sodium chlorite, hydrogen peroxide complexes (such as a PVP-hydrogen peroxide complex) and hydrogen peroxide.

Suitable anticaries agents include but are not limited to a source of fluoride ion. Fluoride sources include sodium fluoride, potassium fluoride, calcium fluoride, stannous fluoride, stannous monofluorophosphate and sodium monofluorophosphate. These sources should release anywhere from about 25 to about 3500 ppm of fluoride ion. The anti-caries agent may be present in an amount from about 0.05% to about 3.0%, preferably about 0.2% to about 1.0% by weight of the dental composition.

Suitable tartar control agents include but are not limited to zinc salts (e.g. zinc citrate trihydrate) and agents containing phosphorous (e.g. sodium tripolyphosphate). Inorganic phosphorous tartar control agents may include any of the pyrophosphates such as disodium pyrophosphate, dipotassium pyrophosphate, tetrapotassium pyrophosphate, tetrasodium pyrophosphate and mixtures thereof. Organic phosphorous compounds that may serve as tartar control agents include polyphosphonates such as disodium ethane-1-hydroxy-1,1-diphosphonate (EHDP), methanediphosphonic acid, and 2-phosphonobutane-1,2,4-tricarboxylic acid. Amounts of the polyphosphate may range from about 0.5% to about 20.0%, preferably from about 1.0% to about 8.0%, optimally from about 1.2% to about 4.5% by weight of the dental composition. As an alternative to phosphates, zinc salts may be utilized as anti-tartar agents. Most preferred is zinc citrate trihydrate. Amounts of the zinc salt may range from about 0.5% to about 20%, preferably from about 1.0 to about 8.0%, optimally from about 2.0% to about 6.0% by weight of the dental composition.

The concentration of therapeutic agent in the dental composition may be about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25%, 25.5%, 26.0%, 26.5%, 27.0%, 27.5%, 28.0%, 28.5%, 29.0%, 295%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50% weight to weight of the composition.

Auxiliary ingredients contemplated to be included in the compositions of the present invention include adhesion promoters, thickeners, secondary film-forming agents, flavorants, humectants, sweeteners, surface active agents, emulsifiers, pH adjusting agents, stabilizing agents, secondary therapeutic agents, opacifying agents, colorants, diluents and other product modifying or enhancing components.

Adhesion promoters could be included to better selectively bind the composition to the teeth instead of the backing layer. Suitable adhesion promoters includes, but is not limited to, polyvinyl pyrollidone, Carbopol®, polycarbophil, Eudragit® polyers and copolymers and Gantrez®.

Suitable thickeners are well-known in the art. Suitable secondary film-forming agents include but are not limited to poly (vinyl pyrrolidone) (PVP), hydroxypropyl cellulose, hydroxyethyl cellulose, and methyl cellulose. Such thickeners and film-forming agents could have the effect of increasing the adhesive strength between the composition and the tooth. These thickeners and film-forming agents could also have an effect on the viscosity of the composition.

Suitable flavorants include but are not limited to oils derived from plants and fruits such as citrus oils, fruit essences, mint, peppermint oil, spearmint oil, capsaicin, clove oil, oil of wintergreen, anise, sassafras, sage, eucalyptus, marjoram, cinnamon, lemon, orange, banana, cherry, apple, pineapple, grape, strawberry, blueberry, tutti frutti, methyl salicylate and the like. It is to be understood that other natural and artificial flavoring agents may be used, other than what is explicitly described in the foregoing.

Suitable humectants include but are not limited to glycerin, sorbitol, xylitol, mannitol, lactitol, maltitol, and other sugar alcohols, polyethylene glycol, propylene glycol, and other edible polyhydric alcohols and mixtures thereof.

Suitable sweeteners include but are not limited to sucrose, lactose, dextrose, maltose, dextrin, dried inverted sugar, fructose, levulose, galactose, corn syrup and their solids, sorbitol, mannitol, xylitol, hydrogenated starch hydrolysates, maltitol, sucralose, aspartame, salts of acesulfame, alitame, saccharin and its salts, cyclamic acid and its salts, glycyrrhizin, dihydrochalcones, thaumatin, monellin, stevia extract and the like.

Suitable surface active agents include but are not limited to sodium lauryl sulfate, condensates of sorbitan mono-oleate with from about 20 to 60 moles of ethylene oxide (e.g., "Tweens" a trademark of ICI United States, Inc.), condensates of ethylene oxide with propylene oxide and condensates of propylene glycol ("Pluronics" a trademark of BASF-Wyandotte Corp.).

Suitable pH adjusting agents include but are not limited to sodium hydroxide, potassium hydroxide, ammonium hydroxide, sodium carbonate, potassium carbonate, TRIS and triethanolamine. While the composition can be at any pH, the pH should be within a range that is physiologically safe for use in the human oral cavity, preferably in the range of about 5.0 to about 9.0.

Suitable stabilizing and/or chelating agents include but are not limited to EDTA and its salts, citric acid and its salts, gluconic acid and its salts, etidronic acid (Dequest® 2010), alkali metal pyrophosphates and alkali metal polyphosphates.

Suitable opacifying agents include but are not limited to titanium dioxide, zinc oxide and hydroxyapatite.

Suitable colorants include but are not limited to FD&C-type dyes and lakes, fruit and vegetable extracts, titanium dioxide, and the like, alone or in combination.

Diluents could be included to decrease the viscosity of the composition. Sample diluents includes: glycerine, propylene glycol, low molecular weight polyethylene glycols and water.

Drying agents could be included to decrease the amount of time it takes for the composition to dry from a liquid to a solid or semi-solid. Any number of bio compatible volatile liquids, for example, alcohol, acetone, hexane and ethyl acetate, could be utilized to create a quicker to dry composition.

The concentration of each auxiliary ingredient in the dental composition may be about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 160%, 16.5%, 17.0%, 17.5%, 18.0%, 18.5%, 19.0%, 19.5%, 20.0% weight to weight of the composition.

Additional carriers, therapeutic agents, and excipients useful in the invention are listed in Remington's, The Science and Practice of Pharmacy (2000); Lieberman et al., Pharmaceutical Dosage Forms (2d ed. 1989); Merck Index (13th Ed.).

Device Manufacture

Deposition of therapeutic composition patterns may be accomplished by contact or non-contact printing or application. A preferred application process is piezoelectric printing, also known as inkjet printing, which allows for the deposition of very small and discrete "islands" or "dots" of material onto planar and non-planar substrates. Dot sizes as small as 5 microns in diameter are possible with certain types of piezoelectric printers, however for the purposes of the invention dot sizes in the range of from about 10 microns to about 2 millimeters, and more particularly from about 100 microns to about 1 millimeter, are preferred, depending upon the particular composition, active ingredient and therapeutic purpose of the inventive micro-patterned device.

FIGS. 1a, 1b, 3 and 4 depict an embodiment of a strip manufactured by printing upon it. Backing layer 1 has micro-patterned composition 2 printed on it. The micro-patterned composition 2 is preferably configured as dots or islands of composition.

When creating a strip by this method, the viscosity of the composition must be such that the composition can be printed. There exists a wide range of printers that would be capable of manufacturing strips by this method. Along with the wide range of printers, there exists a wide range of printable viscosities associated with the various printers. As a result, the actual viscosity of the composition will vary widely depending on the equipment used. Additionally, the composition does not need to limited to the viscosity that a particular printer can print. There are methods to manipulate the viscosity of the composition allowing it to print. For example, the composition could be heated prior to printing, causing a higher viscosity composition to decrease in viscosity while printing, only to increase composition after printing. Another way to print a higher viscosity composition would be to print at a higher pressure. In addition to manipulating the viscosity while printing, diluents, thickeners and film forming agents (see above) can also be used to adjust the viscosity so that it is in the proper range for printing.

An alternative means of manufacturing the inventive micro-patterned device as depicted in FIGS. 1a, 1b, 3 and 4 is through micro-gravure printing whereby a micro-patterned roller is created with wells in the desired shape and size. The roller is contacted with the desired composition through a process called knife coating in which excess material (material not deposited in the micro-patterned wells) is scraped off in a continuous process and the material in the wells is transferred to a backing material through a typical gravure printing process creating the micro-patterned composition 2. For example, a microgravure roller can be made having hemispherical wells 500 microns in diameter and 250 microns deep, each well being spaced 1 millimeter on center from the adjacent well. Such a micro-pattern will result in printed backing material with hemispherical dots of composition with at least 500 micron separation between dots.

FIGS. 2a-2b depicts an alternative embodiment of a strip. In this embodiment, backing layer 1 has a series of wells or pits 4 which create the micro-patterned composition. The backing layer 1 is coating with composition such that the composition fills the wells or pits 4. The excess composition is scraped from backing layer 1, leaving behind composition that has filled the series of wells or pits 4. As a result, the discontinuous micro-patterned composition is formed by the filled wells or pits.

After the composition is applied to the backing layer, the composition is dried or otherwise thickened to either a solid or semi-solid state. The amount of time to for the composition to dry could be decreased in a number of ways. For example, one way to decrease the drying time of the composition would be to include a drying agent in the composition (see above). Other methods of decreasing the drying time include heating the manufactured strip or increasing air circulation over the strip.

The manufactured strip may also need to be cut or trimmed to an appropriate size. Generally the size needs to be large enough to be easily handled by the user, but small enough to fit within the oral cavity.

In an alternative embodiment, the manufactured strips are formed as a continuous backing layer. Composition is transferred to the continuous backing layer by any method capable of creating a discontinuous micro-pattern of composition. The composition is allowed to dry or thicken into a solid or semi-solid state. The continuous backing layer is then would around spools at each end of the continuous backing layer and then placed in a dispensing device (not illustrated).

EXAMPLES

Example 1

The following composition was manufactured on a laboratory scale in a planetary mixer (Model DPM-2, Charles Ross & Sons, Hauppauge, N.Y.) as follows:

| Ingredient | Percent (w/w) |
| --- | --- |
| Deionized water | 13.690 |
| Glycerin | 40.000 |
| Etidronic acid | 0.500 |
| Potassium stannate | 0.020 |
| Hydrogen peroxide 35% | 42.290 |
| Carbopol ® 974P | 2.000 |
| Ammonium Hydroxide 29% | to pH 5.0 |
| Total | 100.000 |

In a suitable plastic container, combine the water and glycerin, followed by the etidronic acid and Potassium stannate, and mixing until dissolved with a plastic or Kynar®-coated mixing impeller. Add the hydrogen peroxide and mix well. Add the Carbopol® 974P all at once, mix with high agitation for at least one hour to disperse and dissolve the powder. Transfer this mixture to a Kynar®-coated 2-gallon double planetary mixer. Neutralize with ammonium hydroxide (added drop-wise through open sight glass) to a pH of 5.0. Mix under vacuum to remove all traces of entrapped air, then package in plastic containers until ready for further processing or use.

The mixture prepared above was placed into the plastic syringe reservoir of a Model MV-100-300 PicoDot® piezo-mechanical printing valve (Nordson EFD, East Providence, R.I.) and centrifuged at 5000 xrpm to remove all traces of entrapped air in order to allow for uninterrupted flow through the printing valve. The valve was mounted on a 3-axis robot (Janome JR200N, Janome Sewing Machine LTD, Tokyo, Japan) with a 200 mm×200 mm print area and 10 micron reproducibility in X, Y and Z coordinates. Printing of micro-patterns was performed at room temperature in all cases.

Figure 3:
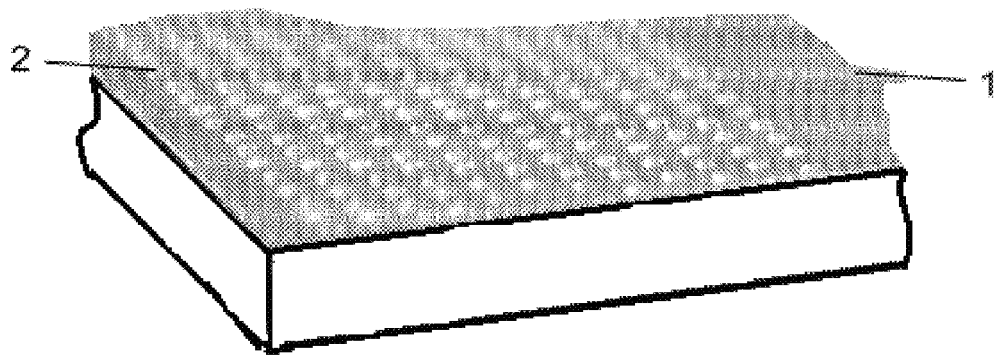
FIG. 3 is an elevated view of a micro-patterned dot array deposited on a backing layer.
Figure 4:
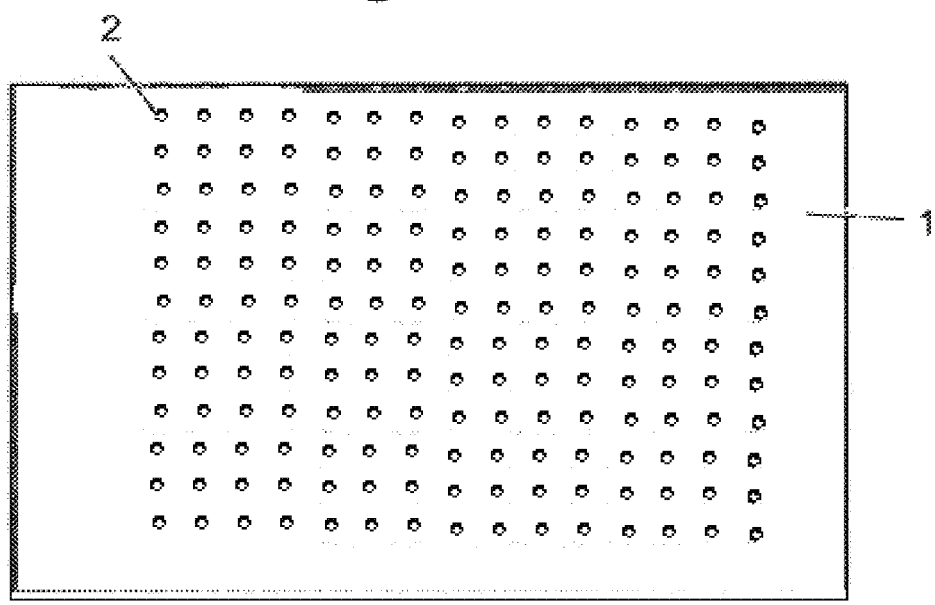
FIG. 4. is a top view of a micro-patterned dot array deposited on a backing layer.

An oversized backing layer comprising a 50 mm×50 mm square of a polyolefin/wax blend film (Parafilm® M, SPI Supplies, West Chester, Pa.) was placed on the robot's positioning platform and secured in place with adhesive tape on all four edges. A micro-pattern comprising a 400 dot array was programmed into the printer to print the dots within a 20 mm×50 mm rectangle (approximating the desired contact area for a single dental arch treatment). The dots printed as well defined hemispheres with an aspect ratio approximating 1× height:2× diameter. The dots were determined by image analysis to be approximately 480 microns in diameter (FIG. 3).

The backing layer was subsequently trimmed to 20 mm×70 mm, allowing for an unprinted edge for handling without contact with the micro-patterned dot array. Such an edge also makes for easier and cleaner handling during strip placement and subsequent array transfer.

Example 2

The following non-limiting table outlines the scope of ingredients having utility in the formulation of tooth whitening compositions useful in conjunction with the inventive devices.

| Actives | Diluents/ Carriers | Adhesion Promoters | Thickeners | Stabilizers | Optional |
|---|---|---|---|---|---|
| Hydrogen peroxide | Glycerin | PVP | PVP | Stannates | Colorants |
| Carbamide peroxide | Polyethylene glycol | Carbopol ® | Carbopol ® | Chelating agents | Flavorants |
| PVP/Hydrogen peroxide complex | Propylene glycol | Polycarbophil | Polycarbophil | | Surfactants |
| Sodium percarbonate | Ethanol | Eudragit ® polymers/ copolymers | Gantrez | | Secondary actives |
| Allyl methacrylates crosspolymer/ Hydrogen peroxide complex | Hydrocarbon oils/waxes | Gantrez | | | Penetrants |
| | Vegetable oils/waxes | | | | Enamel opacifiers PH adjusting agents |
| 0.1-30 (based on hydrogen peroxide) | 20-80 | 0.1-75 | 0.1-75 | 0.001-10 | 0.0001-10 |

What is claimed is:

1. A strip for transferring a therapeutic composition to a tooth comprising:
    a backing layer; and
    at least one therapeutic composition;
    said therapeutic composition is arranged in a discontinuous micro-pattern on said backing layer;
    wherein said backing layer is substantially water insoluble and has a series of pits filled by said therapeutic composition; and
    wherein said therapeutic composition has an adhesion property that has a lower release strength from said backing layer than adhesive strength to a tooth such that contacting said tooth with a portion of said at least one therapeutic composition transfers said portion of said at least one therapeutic composition from said backing layer to said tooth.

2. The strip of claim 1 wherein said backing layer is comprised of at least one layer of material.

3. The strip of claim 2, wherein said backing layer further comprises a release agent.

4. The strip of claim 1, wherein said backing layer is constructed from a material selected from polyethylene, polypropylene, poly ethylene-co-vinyl acetate, polyesters, poly vinyl alcohol, fluoropolymers, film-forming waxes and combinations thereof.

5. The strip of claim 1, wherein said backing layer thickness is less than 1 mm.

6. The strip of claim 1, wherein said backing layer thickness is less than 100 microns.

7. The strip of claim 1, wherein said backing layer has a thickness between about 10 microns to about 50 microns.

8. The strip of claim 1, wherein said at least one therapeutic composition is selected from the group comprising: antimicrobial, tartar control, tooth and gum protectants, teeth whiteners and combinations thereof.

9. The strip of claim 1, wherein said at least one therapeutic composition is in a solid or semi-solid form at room temperature.

10. The strip of claim 1, wherein said discontinuous micro-pattern comprises at least two unconnected therapeutic compositions on said backing layer.

11. The strip of claim 1, wherein said micro-pattern is comprised of hemispheres or islands of said therapeutic composition.

12. The strip of claim 1, wherein said micro-pattern is comprised of hemispheres or islands having a diameter of about 10 microns to about 2 millimeters.

13. The strip of claim 1, wherein said backing layer is coated by said release agent.

14. The strip of claim 1, wherein said therapeutic composition comprises a solid or semi-solid carrier and at least one therapeutic agent.

15. The strip of claim 1, wherein said composition further comprises at least one adhesion promoter.

16. The strip of claim 1, wherein said micro-pattern is comprised of hemispheres having an aspect ratio of 1× height: 2× diameter.

17. The strip of claim 1, wherein said backing layer further comprises a first surface energy and said tooth further comprises a second surface energy, wherein said first surface energy is lower than said second surface energy.

18. The strip of claim 1, wherein said backing layer further comprises a release agent selected from the group comprising waxes, fatty acid metal soaps, long chain alkyl hydrocarbon derivatives, silicone polymers, fluorinated compounds and combinations thereof.

19. The strip of claim 1, wherein said backing layer further comprises a release agent bound to said therapeutic composition.

20. A method for transferring therapeutic compositions to a tooth, the method comprising acts of:
 filling a series of pits in a device comprising at least a backing layer with at least one therapeutic composition having an adhesion property that has a lower release strength from said backing layer than adhesive strength to a tooth, said therapeutic composition arranged in a discontinuous pattern on said backing layer;
bringing into contact the device with at least one tooth such that a portion of said therapeutic composition comes into contact with said at least one tooth;
 removing said backing layer;
 wherein contacting said device with said tooth transfers at least said portion of said therapeutic composition onto said tooth such that said portion of therapeutic composition that is in contact with said tooth remains on said tooth when said backing layer is removed.

21. The method of claim 20, wherein said discontinuous pattern is comprised of hemispheres or islands.

\* \* \* \* \*